(12) United States Patent
Li et al.

(10) Patent No.: US 11,104,681 B2
(45) Date of Patent: Aug. 31, 2021

(54) SOLID FORMS OF TTK INHIBITOR

(71) Applicant: UNIVERSITY HEALTH NETWORK, Toronto (CA)

(72) Inventors: Sze-Wan Li, Toronto (CA); Heinz W. Pauls, Oakville (CA); Peter Brent Sampson, Oakville (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 16/806,392

(22) Filed: Mar. 2, 2020

(65) Prior Publication Data
US 2020/0270259 A1 Aug. 27, 2020

Related U.S. Application Data

(63) Continuation of application No. 16/318,426, filed as application No. PCT/CA2017/050848 on Jul. 13, 2017, now Pat. No. 10,584,130.

(60) Provisional application No. 62/363,424, filed on Jul. 18, 2016.

(51) Int. Cl.
| A61K 31/519 | (2006.01) |
|---|---|
| A61P 35/00 | (2006.01) |
| C07D 487/04 | (2006.01) |
| C30B 29/58 | (2006.01) |
| C30B 7/14 | (2006.01) |
| C30B 7/02 | (2006.01) |

(52) U.S. Cl.
CPC .......... *C07D 487/04* (2013.01); *A61K 31/519* (2013.01); *A61P 35/00* (2018.01); *C30B 7/02* (2013.01); *C30B 7/14* (2013.01); *C30B 29/58* (2013.01); *C07B 2200/13* (2013.01)

(58) Field of Classification Search
CPC ...... A61K 31/519; A61P 35/00; C07D 487/04
See application file for complete search history.

(56) References Cited

U.S. PATENT DOCUMENTS

| 9,573,954 B2 | 2/2017 | Liu et al. |
| 9,657,025 B2 | 5/2017 | Laufer et al. |
| 10,106,545 B2 | 10/2018 | Liu et al. |
| 10,167,289 B2 | 1/2019 | Laufer et al. |
| 10,570,143 B2 | 2/2020 | Liu et al. |
| 10,584,130 B2 | 3/2020 | Li et al. |
| 2019/0322669 A1 | 10/2019 | Laufer et al. |

FOREIGN PATENT DOCUMENTS

| RU | 2417996 C2 | 5/2011 |
| WO | 2006/052913 A1 | 5/2006 |
| WO | WO-2014/075168 A1 | 5/2014 |
| WO | WO-2015/070349 A1 | 5/2015 |

OTHER PUBLICATIONS

U.S. Appl. No. 14/443,072, filed May 15, 2015, U.S. Pat. No. 9,573,954, Issued.
U.S. Appl. No. 15/434,275, filed Feb. 16, 2017, U.S. Pat. No. 10,106,545, Issued.
U.S. Appl. No. 16/155,846, filed Oct. 9, 2018, U.S. Pat. No. 10,570,143, Issued.
U.S. Appl. No. 16/793,542, filed Feb. 18, 2020, Pending.
U.S. Appl. No. 14/626,977, filed Oct. 29, 2015, U.S. Pat. No. 9,657,025, Issued.
U.S. Appl. No. 15/598,402, filed May 18, 2017, U.S. Pat. No. 10,167,289, Issued.
U.S. Appl. No. 16/225,970, filed Dec. 19, 2018, 2019-0322669, Published.
U.S. Appl. No. 16/318,426, filed Jan. 17, 2019, U.S. Pat. No. 10,584,130, Issued.
Liu et al., Discovery of Pyrazolo[1,5-a]pyrimidine TTK Inhibitors: CFI-402257 is a Potent, Selective, Bioavailable Anticancer Agent. ACS Med Chem Lett. May 6, 2016;7(7):671-5. Including Supplementary Materials.
Mason et al., Functional characterization of CFI-402257, a potent and selective Mps1/TTK kinase inhibitor, for the treatment of cancer. Proc Natl Acad Sci U S A. Mar. 21, 2017;114(12):3127-3132.
International Search Report and Written Opinion for Application No. PCT/CA2017/050848, dated Sep. 19, 2017, 13 pages.
Supplementary European Search Report for Application No. 17830139.6, dated Dec. 5, 2019, 8 pages.

(Continued)

*Primary Examiner* — Brenda L Coleman
(74) *Attorney, Agent, or Firm* — McCarter & English, LLP; Steven G. Davis; Wei Song

(57) ABSTRACT

The present invention relates to a novel co-crystal of the compound of formula (I):

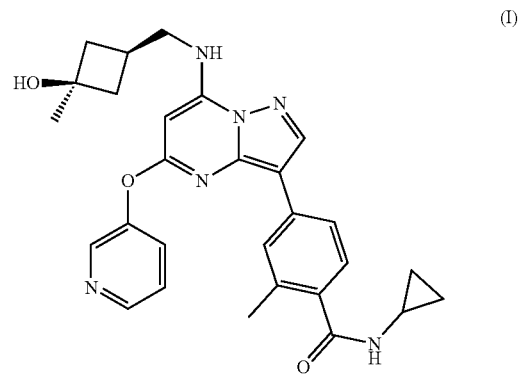

wherein the co-former molecule is bisphosphate hemihydrate, to processes for the preparation of the co-crystal, to pharmaceutical compositions containing the co-crystal, to the use of such a co-crystal in the manufacture of a medicament for use in the treatment of cancer and to methods of treating such diseases in the human or animal body by administering a therapeutically effective amount of such a co-crystal.

19 Claims, 7 Drawing Sheets

(56) References Cited

OTHER PUBLICATIONS

U.S. Appl. No. 16/880,192, filed May 21, 2020, 2021-0009595, Published.
Caira, Crystalline Polymorphism of Organic Compounds. Topics in Current Chemistry. 1998;198;163-208.
Duggirala et al., Pharmaceutical cocrystals: along the path to improved medicines. Chem Commun (Camb). Jan. 14, 2016;52(4):640-55.
Kharkevich, Pharmacology, 10th Edition, GEOTAR-Media Publishers, Moscow. pp. 73-74, (2010).
Zhulenko et al., Pharmacology, KolosS Publishers, Moscow. pp. 34-35, (2008).
Russian Office Action for Application No. 2019101109, dated Feb. 5, 2021, 21 pages.
Takata, Cocrystal Screening and Its Application in Improvements of Physicochemical Properties of API. Pharm Tech Japan. 2009;25(12):155-166.
Ueto, Assessment and Manufacture for Application of Cocrystal to Active Pharmaceutical Ingredient (API) of Medicaments. Pharmacia. 2013;49(12):1201.
Japanese Office Action for Application No. 2019-501928, dated May 11, 2021, 9 pages.

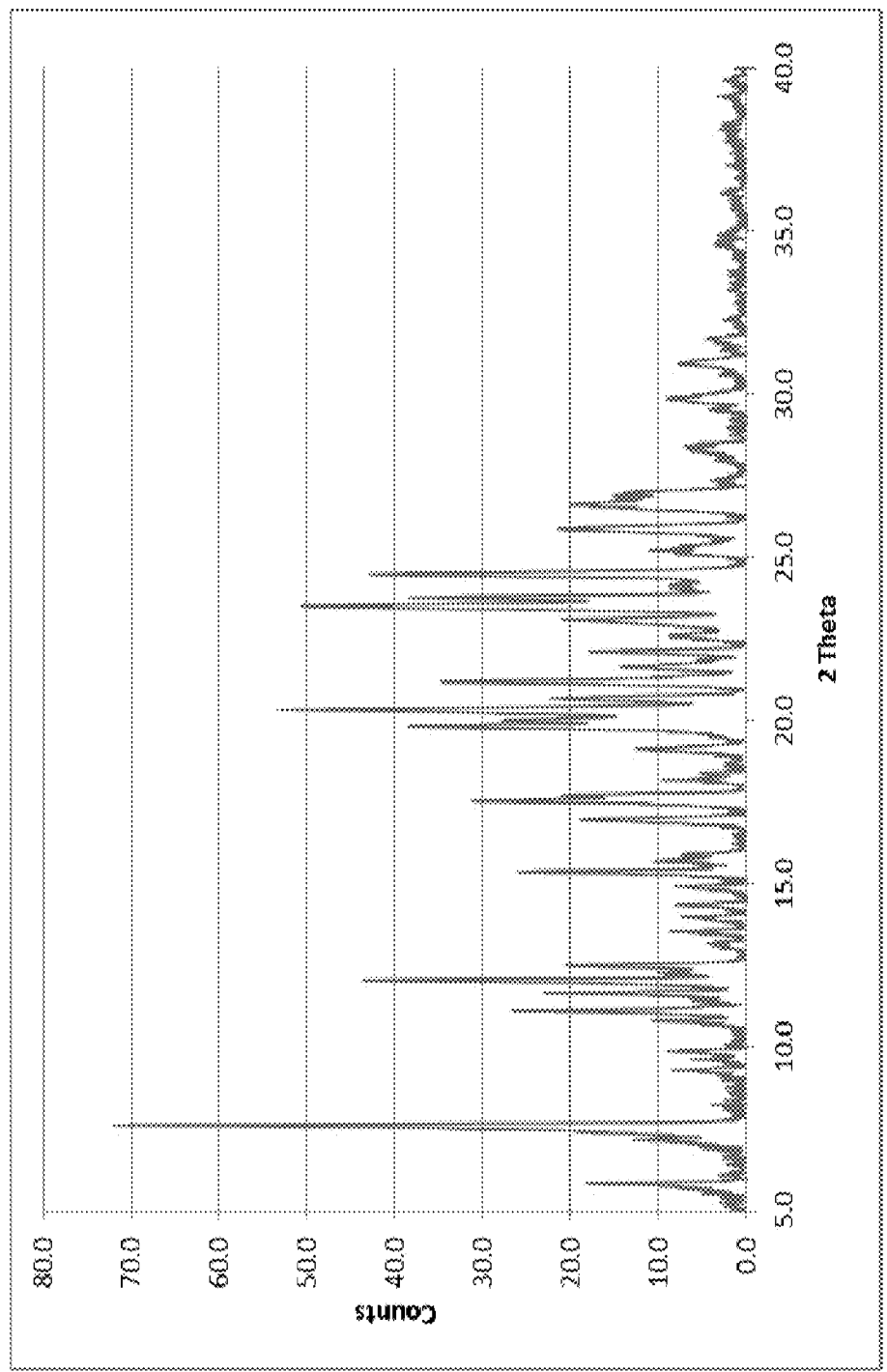
Figure 1. XRPD of Compound (I) Bisphosphate Hemihydrate Co-Crystal

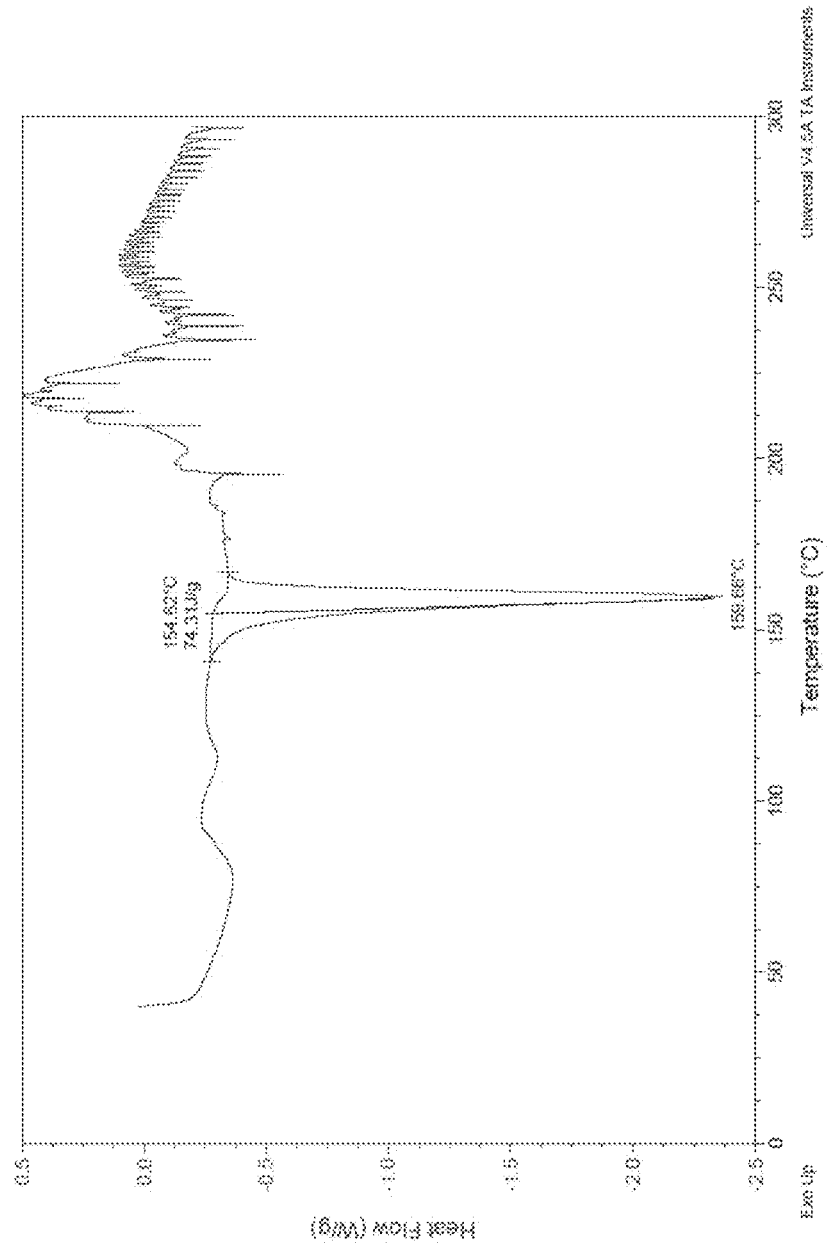
Figure 2. DSC thermogram of Compound (I) Bisphosphate Hemihydrate Co-Crystal Solid State $^{15}$N-NMR Spectra of A) Compound (I) and B) Compound (I) Bisphosphate Hemihydrate Co-Crystal

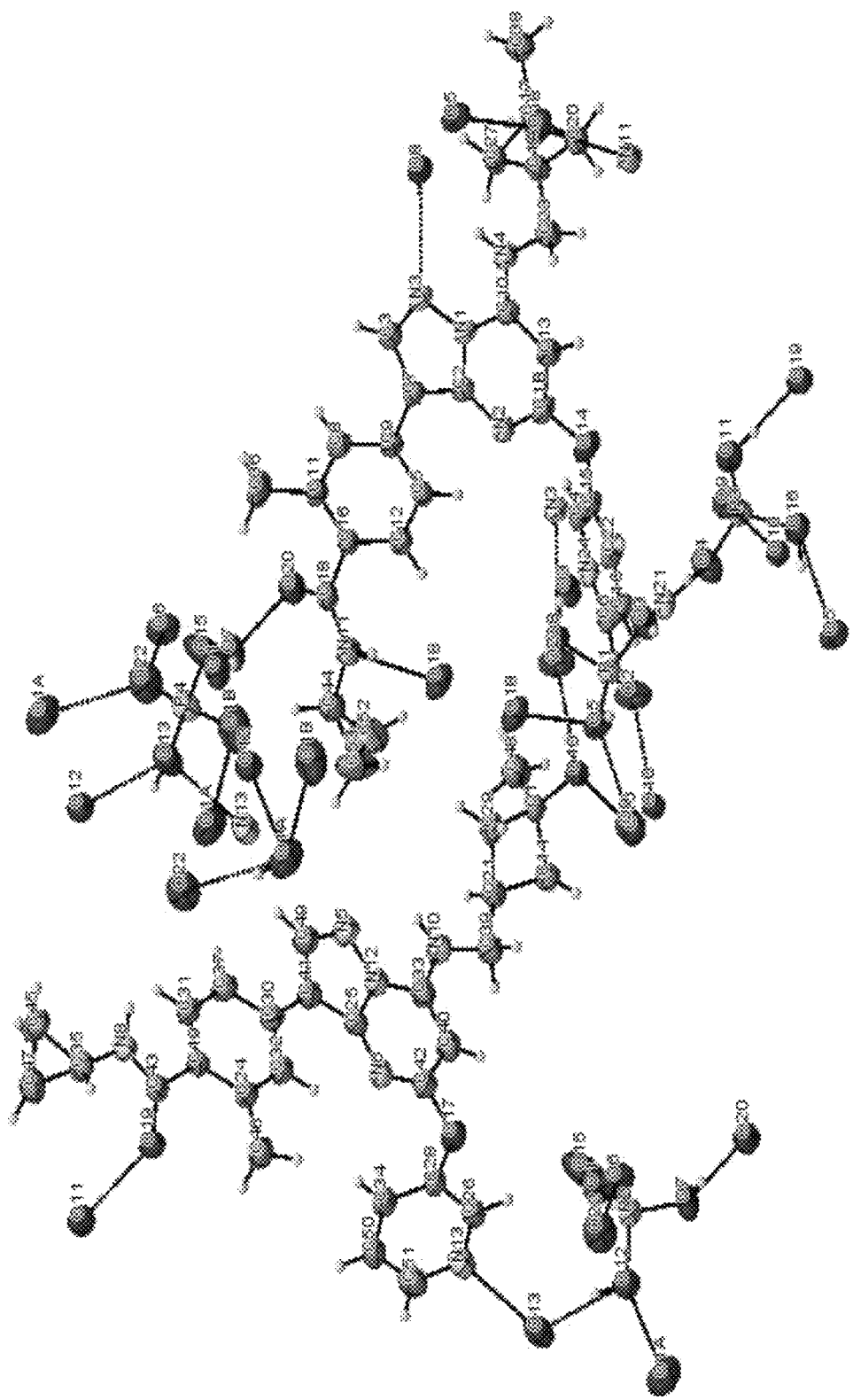
Figure 4. ORTEP Structure of Compound (I) Bisphosphate Hemihydrate Co-Crystal

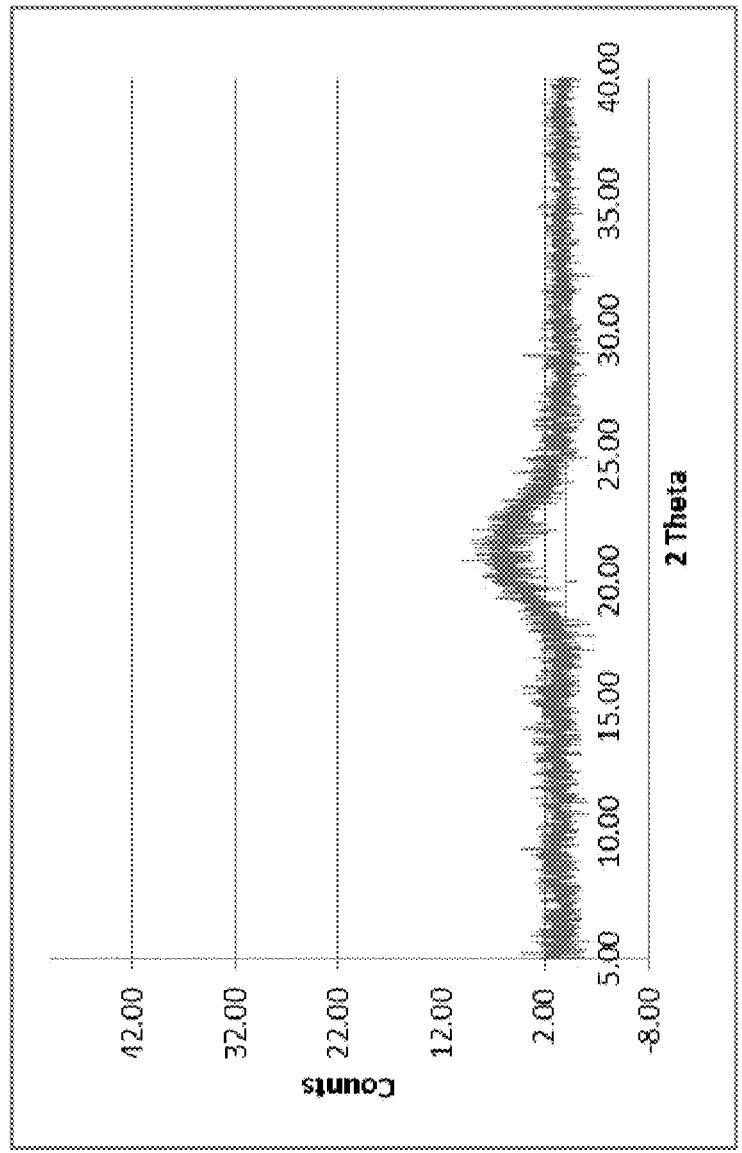
Figure 5. XRPD of Amorphous 1:2 Compound (I)/Phosphoric Acid

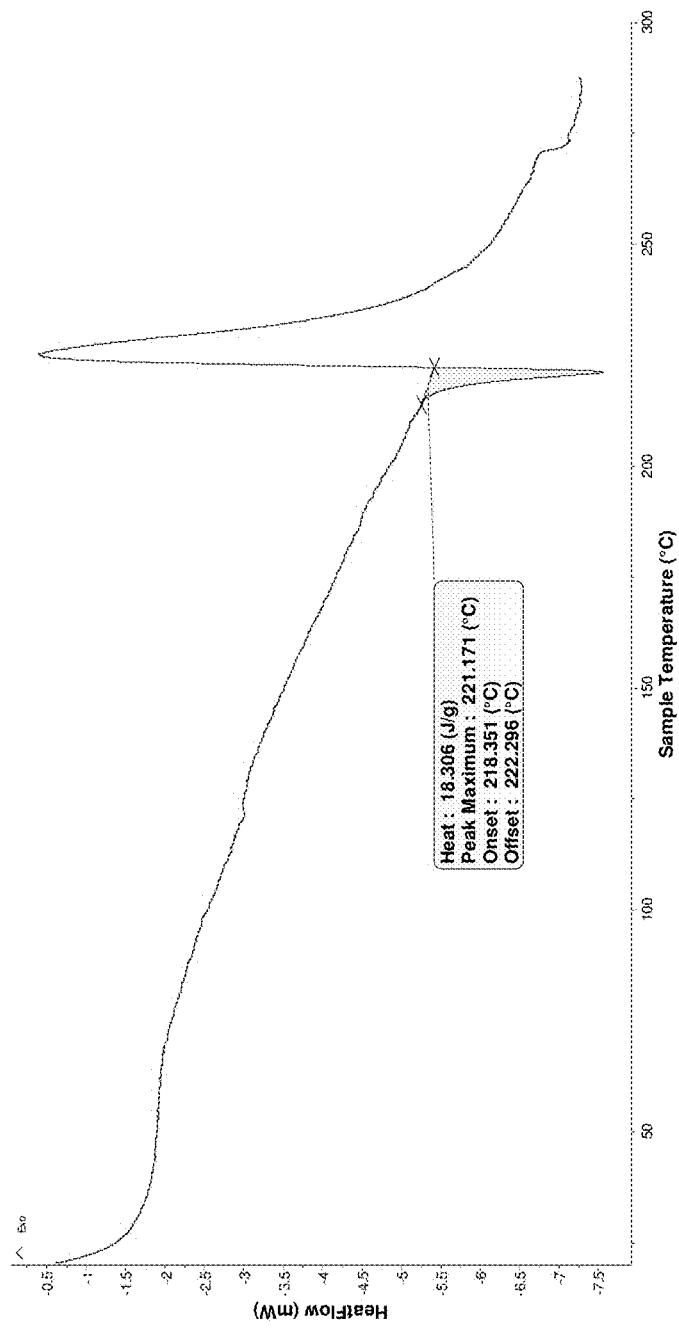
Figure 6. DSC Thermogram of Compound (I) Hydrobromide

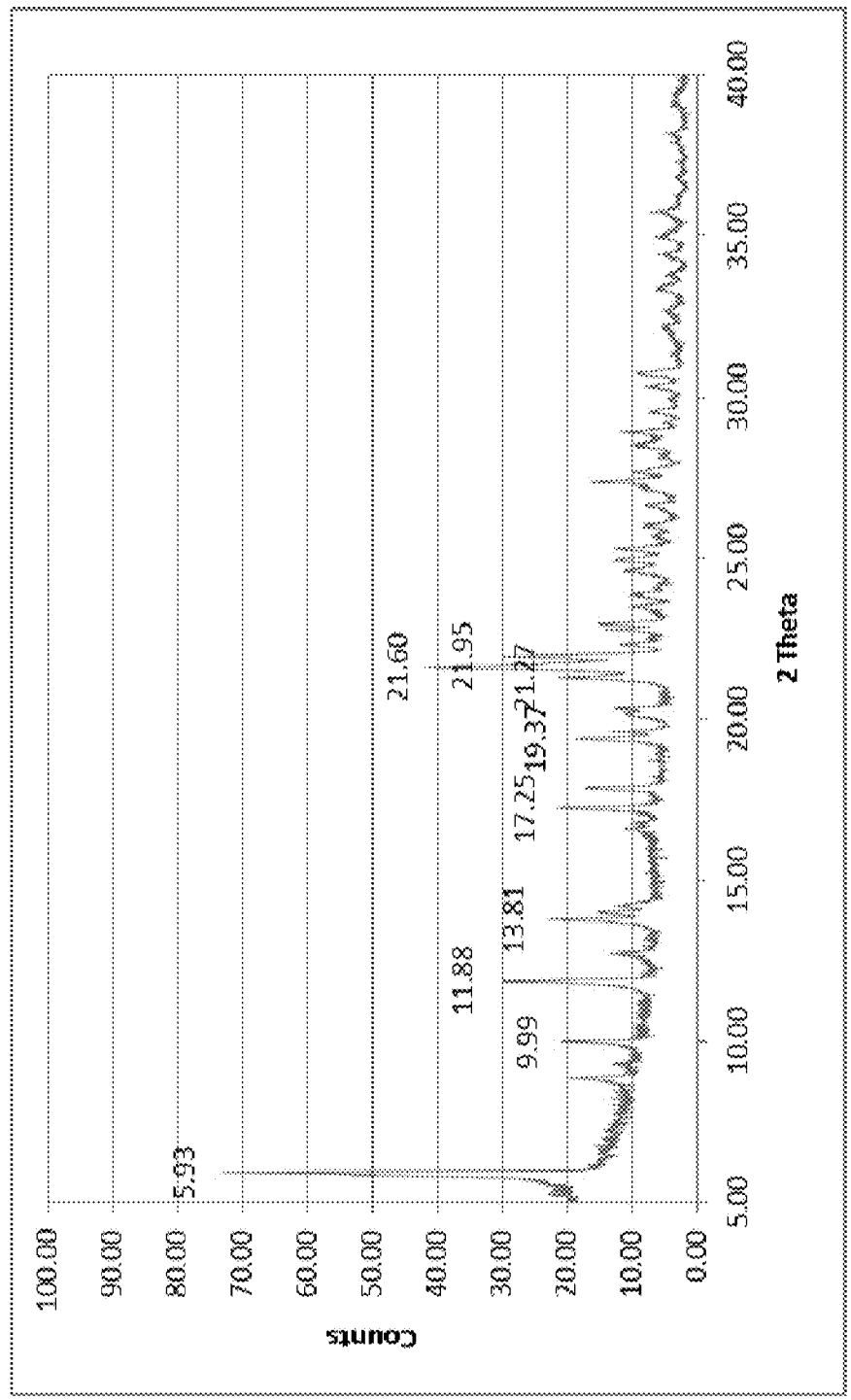
Figure 7. XRPD of Compound (I) Hydrobromide

SOLID FORMS OF TTK INHIBITOR

RELATED APPLICATIONS

This application is a continuation application of U.S. application Ser. No. 16/318,426, filed on Jan. 17, 2019, which is the U.S. national stage application filed under 35 U.S.C. § 371(c), of International Application No. PCT/CA2017/050848, filed on Jul. 13, 2017, which claims the benefit of U.S. Provisional Application No. 62/363,424, filed Jul. 18, 2016. The entire teachings of the aforementioned applications are incorporated herein by reference.

BACKGROUND

Human TTK protein kinase (TTK), also known as tyrosine threonine kinase, dual specificity protein kinase TTK, Monopolar Spindle 1 (Mps1) and Phosphotyrosine-Picked Threonine Kinase (PYT), is a conserved multispecific kinase that is capable of phosphorylating serine, threonine and tyrosine residues when expressed in E. coli (Mills et al., J. Biol. Chem. 22(5): 16000-16006 (1992)). TTK mRNA is not expressed in the majority of physiologically normal tissues in human (Id). TTK mRNA is expressed in some rapidly proliferating tissues, such as testis and thymus, as well as in some tumors (for example, TTK mRNA was not expressed in renal cell carcinoma, was expressed in 50% of breast cancer samples, was expressed in testicular tumors and ovarian cancer samples) (Id). TTK is expressed in some cancer cell lines and tumors relative to normal counterparts (Id.; see also WO 02/068444 A1).

Agents which inhibit TTK have the potential to treat cancer. A number of potent TTK inhibitors are disclosed in International Patent Application Publication Nos. WO 2014/075168 and WO 2015/070349 (the entire teachings of which are incorporated herein by reference). One representative TTK inhibitor is N-cyclopropyl-4-(7-((((1 s,3s)-3-hydroxy-3-methylcyclobutyl)methyl)amino)-5-(pyridin-3-yloxy)pyrazolo[1,5-a]pyrimidin-3-yl)-2-methylbenzamide, the structure of which is reproduced below as compound (I):

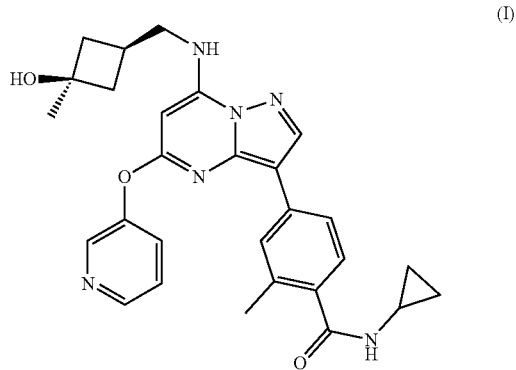 [SMILES: Cc1cc(-c2cnn3c(NC[C@H]4C[C@@](C)(O)C4)cc(Oc4cccnc4)nc23)ccc1C(=O)NC1CC1]

(I)

There is a need for salt forms of this compound that are crystalline and otherwise have physical properties that are amenable to large scale manufacture. There is also a need for pharmaceutical formulations in which this drug candidate is stable and is effectively delivered to the patient.

SUMMARY OF THE INVENTION

The present invention relates to a novel co-crystal of compound (I) and a co-former molecule, wherein the co-former molecule is phosphoric acid. The present invention also relates to a hydrobromide salt of compound (I), wherein the molar ratio between compound (I) and hydrobromic acid is 1:1. Compared to the free base and other salt forms of compound (I), the new solid forms exhibit significantly improved properties including increased water solubility, melting points, and pharmacokinetic exposure. In particular, as shown in Example 5 below, the co-crystal of compound (I) and phosphoric acid and the hydrobromic acid salt of compound (I) in crystalline form result in significantly increased plasma concentrations relative to free base compound (I) in both rats and dogs, following oral administration. This has a major advantage because the new solid forms can be administered orally to result in effective plasma levels of the drug.

In a first embodiment, the present invention is directed to a co-crystal of compound (I) and a co-former molecule, or a solvate of the co-crystal, wherein the co-former molecule is phosphoric acid.

In a second embodiment, the invention provides a co-crystal according to the first embodiment, wherein the molar ratio of compound (I): phosphoric acid in the co-crystal is 1:2.

In a third embodiment, the invention provides a co-crystal according to the first or second embodiment, wherein the co-crystal is a hydrate.

In a fourth embodiment, the invention provides a co-crystal according to the first, second, or third embodiment, wherein the molar ratio of compound (I): phosphoric acid: $H_2O$ in the co-crystal is 1:2:1/2.

In a fifth embodiment, the invention provides a co-crystal according to the first, second, third, or fourth embodiment, wherein the co-crystal is characterized by any three, four, or five of X-ray powder diffraction pattern peaks at 7.60, 12.0°, 20.3°, 23.5°, and 24.5°±0.2 in 2θ.

In a sixth embodiment, the invention provides a co-crystal according to the first, second, third, or fourth embodiment, wherein the co-crystal is characterized by any three, four, five, six, seven, eight, nine, ten, or eleven of X-ray powder diffraction pattern peaks at 7.6°, 11.1°, 12.0°, 15.4°, 17.5°, 19.8°, 20.0°, 20.3°, 21.2°, 23.5°, 23.6°, and 24.5°±0.2 in 2θ.

In a seventh embodiment, the invention provides a co-crystal according to the first, second, third, or fourth embodiment, wherein the co-crystal is characterized by X-ray powder diffraction pattern peaks at 7.6°, 11.1°, 12.0°, 15.4°, 17.5°, 19.8°, 20.0°, 20.3°, 21.2°, 23.5°, 23.6°, and 24.5°±0.2 in 2θ.

In an eighth embodiment, the invention provides a co-crystal according to the first, second, third, or fourth embodiment, wherein the co-crystal is characterized by the X-ray powder diffraction pattern shown in FIG. 1.

In a ninth embodiment, the invention provides a co-crystal according to the first, second, third, fourth, fifth, sixth, seventh, or eighth embodiment, wherein the co-crystal is characterized by differential scanning calorimeter (DSC) peak phase transition temperatures of 160±4° C.

In a tenth embodiment, the invention provides a co-crystal according to the first, second, third, fourth, fifth, sixth, seventh, eighth, or ninth embodiment, wherein a hydrogen bonding is formed between the hydrogen of the phosphoric acid and the nitrogen atom of the pyridine ring of compound (I) and the hydrogen bonding has a distance between 2.5-2.9 Å.

In an eleventh embodiment, the invention provides a co-crystal according to the first, second, third, fourth, fifth, sixth, seventh, eighth, ninth, or tenth embodiment, wherein the co-crystal is characterized by an [15]N-Solid State Nuclear Magnetic Resonance Spectroscopy ($^{15}$N-ssNMR) peak at −122.5±2 ppm, and the intensity of the peak at −122.5 ppm is at least 40-70% less than the peak at −302 ppm. In one embodiment, the intensity of the peak at −122.5 ppm is at least 40%, 50%, 60%, or 70% less than the peak at −302 ppm. In another embodiment, the co-crystal is characterized by the $^{15}$N-Solid State Nuclear Magnetic Resonance Spectroscopy ($^{15}$N-ssNMR) peaks shown in FIG. 3B.

In a twelfth embodiment, the invention provides a pharmaceutical composition comprising the co-crystal according to the first, second, third, fourth, fifth, sixth, seventh, eighth, ninth, tenth, or eleventh embodiment, and a pharmaceutically acceptable carrier or diluent.

In an thirteenth embodiment, the invention provides a hydrobromide salt of compound (I) or a solvate thereof, wherein the molar ratio between compound (I) and hydrobromic acid is 1:1.

In an fourteenth embodiment, the invention provides a hydrobromide salt according to the thirteenth embodiment, wherein the salt is in unsolvated form.

In a fifteenth embodiment, the invention provides a hydrobromide salt according to the thirteenth or fourteenth embodiment, wherein the hydrobromide salt of the present invention is crystalline.

In a sixteenth embodiment, the invention provides a hydrobromide salt according to the fifteenth embodiment, wherein the crystalline hydrobromide salt is characterized by three or four of X-ray powder diffraction pattern peaks at 5.9°, 11.9°, 21.6°, and 22.0°±0.2 in 2θ.

In a seventeenth embodiment, the invention provides a hydrobromide salt according to the fifteenth embodiment, wherein the crystalline hydrobromide salt is characterized by any three, four, five, six, seven, or eight of X-ray powder diffraction pattern peaks at 5.9°, 10.0°, 11.9°, 13.8°, 17.3°, 19.4°, 21.3°, 21.6°, and 22.0°±0.2 in 2θ.

In an eighteenth embodiment, the invention provides a hydrobromide salt according to the fifteenth embodiment, wherein the crystalline hydrobromide salt is characterized by X-ray powder diffraction pattern peaks at 5.9°, 10.0°, 11.9°, 13.8°, 17.3°, 19.4°, 21.3°, 21.6°, and 22.0°±0.2 in 2θ.

In a nineteenth embodiment, the invention provides a hydrobromide salt according to the fifteenth, sixteenth, seventeenth, or eighteenth embodiment, wherein the hydrobromide salt is characterized by X-ray powder diffraction pattern peaks shown in FIG. 7.

In a twentieth embodiment, the invention provides a hydrobromide salt according to the thirteenth, fourteenth, fifteenth, sixteenth, seventeenth, eighteenth, or nineteenth embodiment, wherein the hydrobromide salt is characterized by differential scanning calorimeter (DSC) peak phase transition temperatures of 221±2° C.

In a twenty first embodiment, the invention provides a pharmaceutical composition comprising the hydrobromide salt of according to the thirteenth, fourteenth, fifteenth, sixteenth, seventeenth, eighteenth, nineteenth, or twentieth embodiment, and a pharmaceutically acceptable carrier or diluent.

In one aspect, the present invention provides a method of treating a subject with cancer, comprising administering to the subject an effective amount of the co-crystal according to the first, second, third, fourth, fifth, sixth, seventh, eighth, ninth, tenth, or eleventh embodiment.

In another aspect, the present invention provides a method of treating a subject with cancer, comprising administering to the subject an effective amount of the hydrobromide salt according to the thirteenth, fourteenth, fifteenth, sixteenth, seventeenth, eighteenth, nineteenth, or twentieth embodiment.

Another aspect of the present invention is the use of the co-crystal according to the first, second, third, fourth, fifth, sixth, seventh, eighth, ninth, tenth, or eleventh embodiment for the manufacture of a medicament for treating a subject with cancer.

Another aspect of the present invention is the use of the hydrobromide salt according to the thirteenth, fourteenth, fifteenth, sixteenth, seventeenth, eighteenth, nineteenth, or twentieth embodiment for the manufacture of a medicament for treating a subject with cancer.

Another aspect of the present invention is the co-crystal according to the first, second, third, fourth, fifth, sixth, seventh, eighth, ninth, tenth, or eleventh embodiment for the treatment of cancer.

Another aspect of the present invention is the hydrobromide salt according to the thirteenth, fourteenth, fifteenth, sixteenth, seventeenth, eighteenth, nineteenth, or twentieth embodiment for the treatment of cancer.

BRIEF DESCRIPTION OF THE DRAWINGS

FIG. 1 shows the X-ray Powder Diffraction (XRPD) pattern of Compound (I) Bisphosphate Hemihydrate Co-crystal.

FIG. 2 shows the Differential Scanning Calorimetry Analysis (DSC) thermogram of Compound (I) Bisphosphate Hemihydrate Co-Crystal.

FIG. 4 shows the ORTEP Structure of Compound (I) Bisphosphate Hemihydrate Co-Crystal.

FIG. 5 shows the XRPD pattern of Amorphous 1:2 Compound (I)/Phosphoric Acid.

FIG. 6 shows the DSC thermogram of 1:1 Compound (I) Hydrobromide.

FIG. 7 shows the XRPD pattern of 1:1 Compound (I) Hydrobromide.

DETAILED DESCRIPTION OF THE INVENTION

Figure 3A:
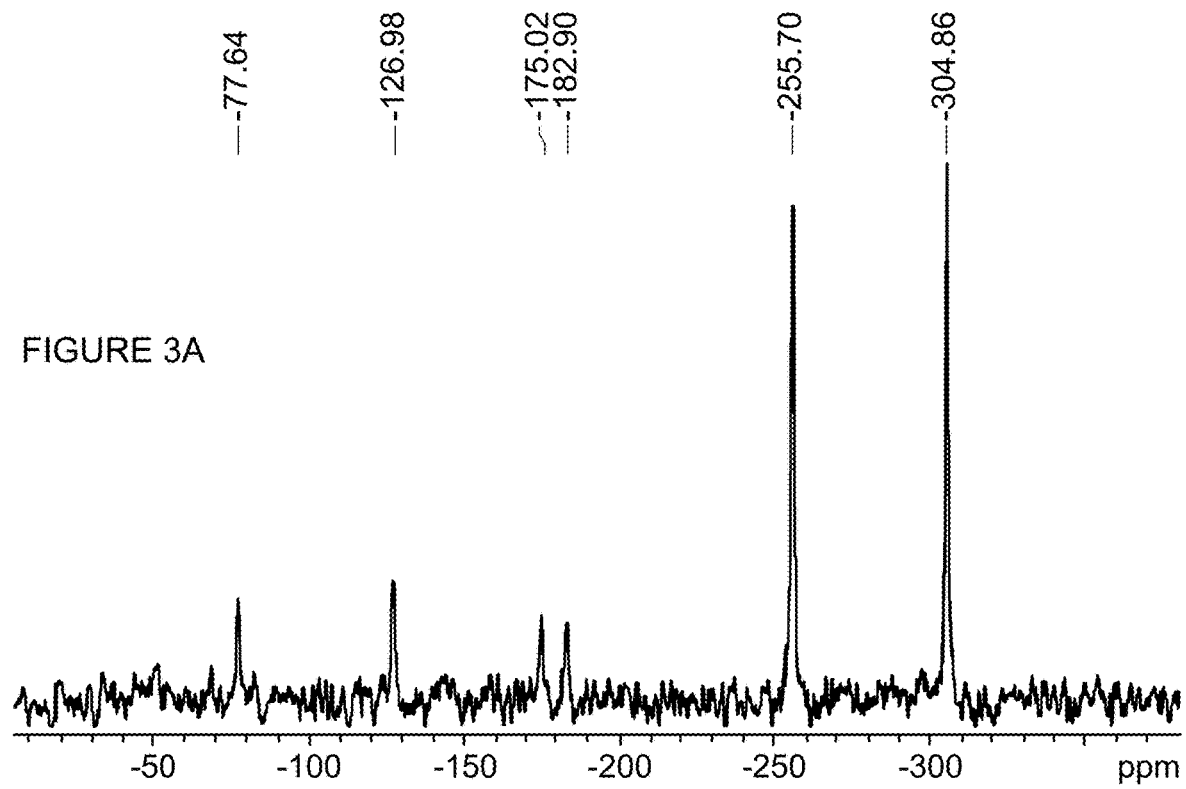
FIGS. 3A and 3B show the Solid State $^{15}$N-NMR Spectra of Compound (I) and Compound (I) Bisphosphate Hemihydrate Co-Crystal, respectively.

The present invention provides new solid forms of compound (I), which is N-cyclopropyl-4-(7-((((1s,3 s)-3-hydroxy-3-methylcyclobutyl)methyl)amino)-5-(pyridin-3-yloxy)pyrazolo[1,5-a]pyrimidin-3-yl)-2-methylbenzamide. Specifically, it has been found that compound (I) and phosphoric acid can form a co-crystal under well-defined conditions to provide a non-hygroscopic crystalline form. It has also been found that the 1:1 hydrobromic acid salt of compound (I) can be crystallized under well-defined conditions to provide non-hygroscopic crystalline forms. Both solid forms provide high bioavailability when administered orally.

The term "co-crystal" (or "cocrystal") refers to a multi-component system in which there exists a host active pharmaceutical ingredient molecule or molecules (API, e.g., compound (I)) and a guest or co-former molecule or molecules (e.g., phosphoric acid). The API and co-former molecules interact by hydrogen bonding and possibly other non-covalent interactions without ionic interactions and without significant or complete proton exchange occurs between the API molecule and the guest molecule. Also included in the invention are solvates, including hydrates of the disclosed co-crystal. In a co-crystal, both the API molecule and the guest (or co-former) molecule exist as a solid at room temperature when alone in their pure form.

"Solvate form" refers to a solid or a crystalline form of compound (I) in free base or a salt, where a solvent molecule is combined with free base compound (I) or the corresponding salt in a definite ratio (e.g., a molar ratio of compound (I):solvent 1:1 or 1:2) as an integral part of the solid or a crystal. "Unsolvated form" refers to a form which is unsolvated, i.e., no definite ratio between a solvent molecule and the free base of compound (I) or the corresponding salt of compound (I), and the solvent molecule is not substantially (e.g., less that 10% by weight) present in the solid form. Well known solvent molecules include water, methanol, ethanol, n-propanol, and isopropanol. The new solid forms disclosed in the present invention include solvated form or unsolvated form.

As used herein, "crystalline" refers to a solid having a crystal structure wherein the individual molecules have a highly homogeneous regular locked-in chemical configuration. Co-crystal of compound (I) and phosphoric acid can be crystals of a single crystalline form of 1:2 compound (I): phosphoric acid, or a mixture of crystals of different single crystalline forms. A single crystalline form means 1:2 compound (I) phosphoric acid as a single crystal or a plurality of crystals in which each crystal has the same crystal form.

Co-Crystal of Compound (I) and Phosphoric Acid

In one embodiment of the invention, there is provided Compound (I): phosphoric acid co-crystal with a molar ratio of approximately 1:2 (see Examples herein). The invention also encompasses the co-crystal in other molar ratios of Compound (I): phosphoric acid.

In another embodiment, the co-crystal of the present invention is in a solvate form (e.g., water). In one particular embodiment, the molar ratio of the co-crystal is as follows: the compound (I)×2 phosphoric acid×1/2 H$_2$O.

In another embodiment, at least a particular percentage by weight of co-crystal of compound (I) and phosphoric acid is a single crystalline form. Particular weight percentages include 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a weight percentage of 70%-75%, 75%-80%, 80%-85%, 85%-90%, 90%-95%, 95%-100%, 70-80%, 80-90%, 90-100%. For example, in a particular embodiment, at least 80% (e.g., at least 90% or 99%) by weight of the particular is in a single crystalline form. It is to be understood that all values and ranges between these values and ranges are meant to be encompassed by the present invention.

When a particular percentage by weight of co-crystal of 1:2 compound (I) and phosphoric acid is a single crystalline form, the remainder of the co-crystal is some combination of amorphous compound (I)/phosphoric acid, and/or one or more other crystalline forms of compound (I)/phosphoric acid excluding the single crystalline form.

In 1:2 compound (I) and phosphoric acid co-crystal, compound (I) is at least 60%, 70%, 80%, 90%, 99% or 99.9% by weight pure relative to the other stereoisomers, i.e., the ratio of the weight of the stereoisomer over the weight of all the stereoisomers.

Crystalline Forms of 1:1 Compound (I) Hydrobromide

In one embodiment of the present invention, there is provided Compound (I) hydrobromide acid with a molar ratio of approximately 1:1 (see Examples herein). In one embodiment, at least a particular percentage by weight of 1:1 compound (I) hydrobromide is crystalline.

In another particular embodiment, at least a particular percentage by weight of 1:1 compound (I) hydrobromide is a single crystalline form. Particular weight percentages include 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a weight percentage of 70%-75%, 75%-80%, 80%-85%, 85%-90%, 90%-95%, 95%-100%, 70-80%, 80-90%, 90-100%. For example, in one embodiment, at least 80% (e.g., at least 90% or 99%) by weight of the 1:1 compound (I) hydrobromide is in a single crystalline form. It is to be understood that all values and ranges between these values and ranges are meant to be encompassed by the present invention.

Crystalline 1:1 compound (I) hydrobromide can be crystals of a single crystalline form of 1:1 compound (I) hydrobromide, or a mixture of crystals of different single crystalline forms. A single crystalline form means 1:1 compound (I) hydrobromide as a single crystal or a plurality of crystals in which each crystal has the same crystal form.

When a particular percentage by weight of 1:1 compound (I) hydrobromide is a single crystalline form, the remainder of the 1:1 compound (I) hydrobromide is some combination of amorphous 1:1 compound (I) hydrobromide, and/or one or more other crystalline forms of 1:1 compound (I) hydrobromide excluding the single crystalline form.

In the 1:1 compound (I) hydrobromide, compound (I) is at least 60%, 70%, 80%, 90%, 99% or 99.9% by weight pure relative to the other stereoisomers, i.e., the ratio of the weight of the stereoisomer over the weight of all the stereoisomers.

Preparation of Crystalline Forms of 1:1 Compound (I) Hydrobromide and Co-Crystal of Compound (I) and Phosphoric Acid The particular solid forms of 1:1 compound (I) hydrobromide and co-crystal of compound (I) and phosphoric acid can be prepared, for example, by slow evaporation, slow cooling, and antisolvent precipitation.

As used herein, "anti-solvent" refers to a solvent, in which 1:1 compound (I) hydrobromide or co-crystal of compound (I) and phosphoric acid has low solubility and causes the bromide salt or co-crystal to precipitate out of solution in the form of fine powder or crystals.

Alternatively, the 1:1 compound (I) hydrobromide (or compound (I) and phosphoric acid co-crystal) can be recrystallized from a suitable solvent with or without the addition of a seed crystal.

In one embodiment, the present invention provides a method of preparing a co-crystal of compound (I) and phosphoric acid, the method comprising:

mixing a suspension of compound (I) and phosphoric acid in a suitable solvent; and removing the solvent. The suitable solvent includes, but not limited to, acetone, diethyl ether, MeOH/THF, acetic acid and 1,4-dioxane. When MeOH/THF are used in the preparation method, the ratio between the two solvents is 3:2 to 2:3 (V:V).

In one embodiment, the molar ratio between compound (I) and phosphoric acid used in the preparation is 1:2 to 1:8.

In one embodiment, the present invention provides a method of preparing 1:1 compound (I) hydrobromide. Specifically, to a suspension of compound (I) in a suitable solvent (e.g., butanol and/or MEK), was added a solution of HBr (e.g., in a solution of butanol and/or MEK); the mixture was heated at 60° C. for 2 hours and then 5° C. overnight. The solid was then recovered by filtration. The suitable solvent includes, but not limited to, butanol and/or MEK, and/or water.

The preparation of each specific solid form is described in the experimental section below.

Methods of Treatment

Another aspect of the present teachings relates to a method of treating a subject with cancer comprising administering to the subject an effective amount of a co-crystal of compound (I) and phosphoric acid (or a hydrobromide salt of compound (I)) described herein. In one embodiment, the co-crystals (or the hydrobromic acid salts of compound (I)) described herein inhibit the growth of a tumor. For example, the co-crystals (or the hydrobromic acid salts of compound (I)) described herein inhibit the growth of a tumor that overexpresses TTK.

Cancers that can be treated (including reduction in the likelihood of recurrence) by the methods of the present teachings include lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In one embodiment, the cancer is selected from leukemia, acute myeloid leukemia, chronic myelogenous leukemia, breast cancer, brain cancer, colon cancer, colorectal cancer, head and neck cancer, hepatocellular carcinoma, lung adenocarcinoma, metastatic melanoma, pancreatic cancer, prostate cancer, ovarian cancer and renal cancer. In one embodiment, the cancer is lung cancer, colon cancer, brain cancer, neuroblastoma, prostate cancer, melanoma, glioblastoma multiform or ovarian cancer. In another embodiment, the cancer is pancreatic cancer, prostate cancer, lung cancer, melanoma, breast cancer, colon cancer, or ovarian cancer. In yet another embodiment, the cancer is breast cancer, colon cancer and ovarian cancer. In yet another embodiment, the cancer is a breast cancer. In yet another embodiment, the cancer is a basal sub-type breast cancer or a luminal B sub-type breast cancer. In yet another embodiment, the cancer is a basal sub-type breast cancer that overexpresses TTK. In yet another embodiment, the basal sub-type breast cancer is ER (estrogen receptor), HER2 and PR (progesterone receptor) negative breast cancer. In yet another embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

As used herein, "treating a subject with a cancer" includes achieving, partially or substantially, one or more of the following: arresting the growth, reducing the extent of the cancer (e.g., reducing size of a tumor), inhibiting the growth rate of the cancer, ameliorating or improving a clinical symptom or indicator associated with the cancer (such as tissue or serum components) or increasing longevity of the subject; and reducing the likelihood of recurrence of the cancer.

As used herein, the term "reducing the likelihood of recurrence of a cancer" means partially or totally inhibiting, delaying the return of a cancer at or near a primary site and/or at a secondary site after a period of remission. It also means that the cancer is less likely to return with treatment described herein than in its absence.

As used herein, the term "remission" refers to a state of cancer, wherein the clinical symptoms or indicators associated with a cancer have disappeared or cannot be detected, typically after the subject has been successfully treated with an anti-cancer therapy.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

The term an "effective amount" means an amount when administered to the subject which results in beneficial or desired results, including clinical results, e.g., inhibits, suppresses or reduces the cancer (e.g., as determined by clinical symptoms or the amount of cancer cells) in a subject as compared to a control.

In an embodiment, an effective amount of 1:1 compound (I) hydrobromide (or compound (I) and phosphoric acid co-crystal) ranges from about 0.01 to about 1000 mg/kg body weight. The skilled artisan will appreciate that certain factors may influence the dosage required to effectively treat a subject suffering from cancer and these factors include, but are not limited to, the severity of the disease or disorder, previous treatments, the general health and/or age of the subject and other diseases present.

Moreover, a "treatment" regime of a subject with an effective amount of the compound of the present invention may consist of a single administration, or alternatively comprise a series of applications. For example, the 1:1 compound (I) hydrobromide (or compound (I) and phosphoric acid co-crystal) may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present invention, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds of the invention can be administered to a patient in a variety of forms depending on the selected route of administration, as will be understood by those skilled in the art. The compounds of the invention may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

Pharmaceutical Compositions

The 1:1 compound (I) hydrobromide (or compound (I) and phosphoric acid co-crystal) disclosed herein can be suitably formulated into pharmaceutical compositions for administration to a subject.

In one embodiment, the present invention provides a pharmaceutical composition comprising the 1:1 compound (I) hydrobromide (or compound (I) and phosphoric acid co-crystal) as described above, and a pharmaceutically acceptable carrier or diluent.

The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

The invention is illustrated by the following examples, which are not intended to be limiting in any way.

EXPERIMENTAL

Abbreviations

BSA benzene sulfonic acid
DSC differential scanning calorimetry
Equiv equivalent
NA not available
NMP N-methyl-2-pyrrolidone
pTSA para-toluenesulfonic acid
RH relative humidity
rt room temperature
temp temperature
TGA thermogravimetric analysis
THF tetrahydrofuran
wt % percent by weight
XRPD X-ray powder diffraction Analysis Conditions
X-Ray Powder Diffraction (XRPD)

XRPD analysis was carried out using a Bruker D8 Discover diffractometer with DAVINCI configuration, scanning the samples between 1.5 and 45° 2θ angles. Approximately, 1-2 mg of each screening sample was used.

Single Crystal X-Ray Diffraction (SC-XRD)

SC-XRD analysis was performed at 293 K on a X-Calibur diffractometer from Oxford Diffractions with Mo Kα source and graphite monochromator. Structure solutions and refinement were performed using SHELXS-97 and SHELXL-97 respectively.

Thermo-Gravimetric/Differential Scanning Calorimetry Analysis (TGA/DSC)

3-10 mg of material was weighted into an open aluminum pan and loaded into a simultaneous Setaram LABSYS EVO thermo-gravimetric/differential scanning calorimeter (TGA-DTA/DSC) with robot, and held at rt. The sample was then heated at a rate of 10° C./min from 30° C. to 350° C. during which time the change in sample weight was recorded along with any differential thermal events. Nitrogen was used as the purge gas, at a flow rate of 100 cm$^3$/min. Prior to the analysis, the instrument was weighed and temperature calibrated using a 100 mg reference weight and an indium reference standard, respectively. Sample analysis was carried out with the help of CALISTO software, where the corresponding mass loss and temperatures of thermal events were quoted as the onset temperature, measured according to the manufacturer's specifications. All analyses were carried out with a heating rate of 10° C./min and background was subtracted.

Differential Scanning Calorimetry (DSC)

1-4 mg of material was weighted into an aluminum DSC pan and sealed non-hermetically with an aluminum lid. The sample pan was then loaded into a TA Instruments Q2000 (equipped with a cooler). Once a stable heat-flow response was obtained at 35° C., the sample and reference were heated to 300° C. at a rate of 10° C./min and the resulting heat flow response was monitored. Prior to analysis, the instrument was temperature and heat-flow calibrated using an indium reference standard. Sample analysis was carried out with the help of TA Universal Analysis 2000 software where the temperatures of thermal events were quoted as the onset and peak temperature, measured according to the manufacturer's specifications.

$^1$H-Nuclear Magnetic Resonance Spectroscopy ($^1$H-NMR)

Nuclear magnetic resonance measurements were recorded on a Bruker Advance DRX 400 instrument at 400 MHz and rt, using DMSO-$d_6$ or CD$_3$OD as solvent without internal standard.

$^{15}$N-Solid State Nuclear Magnetic Resonance Spectroscopy ($^{15}$N-ssNMR)

$^{15}$N Solid state nuclear magnetic resonance analysis was performed on a 500 MHz Bruker Advance III solid-state spectrometer. $^{15}$N spectra were acquired by means of CP-MAS (Cross Polarization under Magic Angle Spinning) on a Bruker 4 mm probe head, two RF channels and sample rotation frequency was 7 kHz.

Example 1: Combinatorial Salt Screen

A salt screen was performed using six solvents (H$_2$O, DMSO, 1,4-dioxane, acetic acid, MeOH/THF (1:1), 1-BuOH/MEK 1:1, and NMP) and twelve pharmaceutically acceptable acids (HCl, HBr, H$_3$PO$_4$, H$_2$SO$_4$, pTSA, BSA, naphthalene sulfonic acid, ethane sulfonic acid, methane sulfonic acid, ethane disulfonic acid, L-maleic acid, and 2-aminosulfonic acid).

The acids were charged to compound (I) (15 mg, solution or slurry in a given solvent) either as solids or as a 10% solution in the appropriate solvent. For all solvents except NMP, acid-base ratios of 1.05:1 and 2.2:1 were employed. For experiments with NMP experiments only the 2.2:1 molar ratio was used. The resulting solutions were aged at RT overnight. Solids were harvested and analyzed. The remaining solutions were either cooled or treated with anti-solvent. If no precipitation occurred after the cooling/anti-solvent treatments, the solutions were vacuum dried. Finally, all recovered solids were placed in a climate chamber at 40° C. and 75% RH for 5 days and reanalyzed. Suitable solvent and counterion combinations were then revaluated for salt formation with compound (I) at an increased scale.

Crystalline material was obtained with eleven of the twelve counterions examined. Experiments with 2-aminosulfonic acid resulted only in recovery of free base material. Multiple crystalline forms were obtained from HCl, methanesulfonic acid, ethane disulfonic acid and p-TSA experiments. Stress testing resulted in conversion to additional crystalline forms, indicating a propensity for polymorphism. Salts obtained from maleic acid experiments were solvated, of low crystallinity and decomposed during DSC analysis. Salts obtained from naphthalene sulfonic acid, benzene sulfonic acid and sulfuric acid were highly hygroscopic.

Crystalline material obtained from experiments with hydrobromic acid and phosphoric acid were shown to have increased solubility relative to free base, low hygroscopicity and were stable under stressed conditions (40° C./75%, RH, 80° C., ambient light for 7 days). Both solid forms were degraded under oxidative stress (3% aq. H$_2$O$_2$). The properties of each isolated crystalline form are outline in Table 1.

TABLE 1

Properties of Crystalline Forms of Compound (I)

| Solid Form | pH$_{max}$ | Solubility$_{max}$ (mg/mL) | Melting Range (DSC) | Hygroscopicity (water sorption at 90% RH) |
|---|---|---|---|---|
| Compound I | NA | <0.001 | 206-210° C. | 0.8% |
| Compound I-monohydrate | NA | <0.001 | 185-190° C. | NA |
| Hydrobromide | 0.79 | 0.63 | 218-221° C. | 2.3% |
| Bisphosphate hemihydrate | <1.14 | 0.10 | 156-163° C. | 3.9% |

Example 2: Preparations of Co-Crystal of 1:2 Compound (I)/Phosphoric Acid

Method A: Compound (I) (605.5 mg, 1 equiv) was slurried in acetone (14 mL). The slurry was stirred at rt for 5 min to allow homogenization. Next, a solution of H$_3$PO$_4$ (459.46 mg, 4 equiv) in acetone (6 mL) was rapidly added. A yellow gel was obtained, and the mixture was kept at rt under stirring for 2 d. The precipitate then filtered, washed with acetone (20 mL) and dried at 4° C./10 mbar. The solid obtained was further characterized as a bisphosphate hemihydrate by TGA, XRPD, DSC, 1H NMR, solid state $^{15}$N NMR, IR, Raman, and single crystal X-ray crystallography.

Method B: a solution of H$_3$PO$_4$ (494.7 g, 4 equiv) in MeOH/THF (10.5 ml, 1:1 v/v) was added to a vial containing compound (I) (506.88 mg, 1 equiv). The resulting mixture was stirred at rt until a yellow solution was obtained. The solution was allowed to evaporate at 50° C. and atmospheric pressure under stirring with the aid of a vortex. A yellow gel was obtained and acetone was then added (15 mL) and let to vortex at rt for 1 d. The slurry was let to stir for additional 3 d. Crystalline solids were then filtered and further characterized as identical in crystal form to the material obtained in Method A.

$^1$H NMR (400 MHz, CD$_3$OD) δ 8.53-8.58 (m, 1H), 8.46-8.50 (m, 1H), 8.36 (s, 1H), 7.80-7.86 (m, 1H), 7.72-7.76 (m, 1H), 7.55-7.61 (m, 2H), 7.18 (d, J=8.0 Hz, 1H), 5.92 (s, 1H), 3.52 (d, J=6.8 Hz, 2H), 2.77-2.86 (m, 1H), 2.28-2.38 (m, 1H), 2.25 (s, 3H), 2.18-2.24 (m, 2H), 1.88-1.99 (m, 2H), 1.37 (s, 3H), 0.75-0.84 (m, 2H), 0.54-0.64 (m, 2H).

TABLE 2

XRPD of Compound (I) Bisphosphate Hemihydrate

| 2θ angle | Relative Intensity (%) |
|---|---|
| 7.6 | 100 |
| 11.1 | 38 |
| 12.0 | 57 |
| 15.4 | 36 |
| 17.5 | 43 |
| 19.8 | 53 |
| 20.0 | 36 |
| 20.3 | 74 |
| 21.2 | 49 |
| 23.5 | 71 |
| 23.6 | 54 |
| 24.5 | 60 |

Single crystal X-ray crystallography data of the phosphate complex of compound (I) indicates that each unit cell contains 2 molecules of Compound (I), 4 molecules of phosphoric acid and 1 molecule of water. The hydrogen bonds within the complex all measure between 2.5-2.9 Å, indicating that there is no ionic character observed between phosphoric acid protons and the basic nitrogen of the pyridine ring. This result is consistent with observations from solid state $^{15}$N-NMR. Taken together, these results confirm the form of Compound (I) bisphosphate hemihydrate as a co-crystal complex. The crystallographic data for Compound (I) bisphosphate hemihydrate is presented in Table 3. The ORTEP representation is presented in FIG. 4.

TABLE 3

Crystallographic data for Compound I Bisphosphate Hemihydrate

| Chemical formula | $(C_{28}H_{30}N_6O_3)$-$2(H_3PO_4)$-$0.5H_2O$ |
|---|---|
| Crystal system | Triclinic |
| Space group | P-1 |
| a (Å) | 9.2631(4) |
| b (Å) | 15.1919(6) |
| c (Å) | 23.4073(10) |
| α (°) | 86.408(3) |
| β (°) | 82.589(3) |
| γ (°) | 87.818(3) |
| V (°) | 3258.54 |
| Z | 2 |
| R-factor (%) | 5.51 |

Figure 3B:
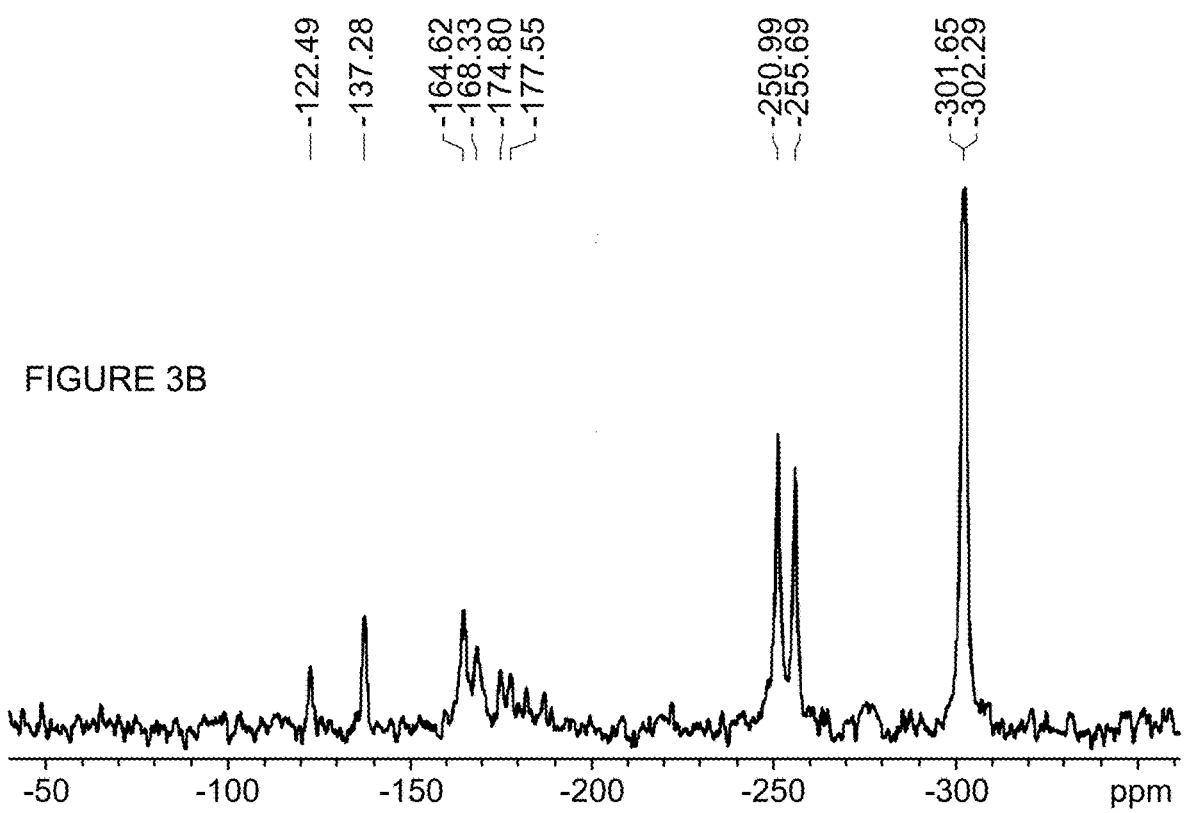

Solid state $^{15}$N-NMR analysis was performed on Compound (I) free base and Compound (I) bisphosphate hemihydrate. Superimposed spectra are presented in FIG. 3. The shift and relative intensity of the pyridine nitrogen peak in the phosphate compound relative to the free base indicates the nature of the interaction between the atoms is hydrogen bonding and does not possess ionic character. No proton transfer to pyridyl nitrogen was discerned, thus confirming the phosphate is a co-crystal.

Compound (I) bisphosphate hemihydrate can also be generated by crystallization of amorphous or semi-crystalline co-crystal of compound (I) and $H_3PO_4$ using the conditions shown in Table 4. Alternatively, crystallization of the viscous gel can be induced to give Compound (I) bisphosphate hemihydrate by depositing the gel along with small amount of solids on a larger glass surface and scratching it with a spatula. Also, the gel can be crystallized by sonication.

TABLE 4

Crystallization of Compound (I) Bisphosphate Hemihydrate

| Solvent system | Temperature (° C.) | RH (%) |
|---|---|---|
| MeOH/THF (1:1 V/V) | 40 | 75 |
| Acetone | rt | — |
| Diethyl ether | 30 | — |

Example 3: Preparation of Amorphous 1:2 Compound (I)/Phosphoric Acid

To a mixture of MeOH/THF (9.7 mL, 1:1 V/V) was added compound (I) (500 mg, 1 equiv) in a glass vial at rt. $H_3PO_4$ (238 mg, 2 equiv) was then added and the resulting mixture was stirred at rt for 2 h. The solution changed color, but no precipitation occurred. The clear solution was then let to stand for 1 d at 5° C. and then for 1 d at −20° C. No solids were obtained. The solvent was then removed at 30° C./10 mbar, and the resulting solids were analyzed by XRPD and were shown to be amorphous solids. 1H NMR (400 MHz, CD$_3$OD) δ 8.53-8.58 (m, 1H), 8.46-8.50 (m, 1H), 8.36 (s, 1H), 7.80-7.86 (m, 1H), 7.72-7.76 (m, 1H), 7.55-7.61 (m, 2H), 7.18 (d, J=8.0 Hz, 1H), 5.92 (s, 1H), 3.52 (d, J=6.8 Hz, 2H), 2.77-2.86 (m, 1H), 2.28-2.38 (m, 1H), 2.25 (s, 3H), 2.18-2.24 (m, 2H), 1.88-1.99 (m, 2H), 1.37 (s, 3H), 0.75-0.84 (m, 2H), 0.54-0.64 (m, 2H).

Amorphous material can also be obtained dissolving Compound (I) into 1,4-dioxane and adding ethyl acetate or acetone as an antisolvent or dissolving Compound (I) into 1-ethoxyethanol and added ethyl acetate as an antisolvent.

Example 4: Preparation of 1:1 Compound (I)/HBr Crystalline Salt

To a mixture of 1-butanol and MEK (60 mL, 1:1 V/V) was added compound (I) (502 mg, 1 equiv). The slurry was heated at 60° C. and HBr (4.8% solution in 1-butanol and MEK (2.5 mL, 2 equiv) was added. The mixture was stirred at 60° C. for 2 h and then 5° C. overnight. The solid was then recovered by filtration, washed with diethyl ether and characterized as a hydrobromide by XRPD, TGA, IR, Raman and DSC.

TABLE 5

XRPD of Compound (I) Hydrobromide

| 2θ angle | Relative Intensity (%) |
|---|---|
| 5.9 | 100 |
| 10.0 | 27 |
| 11.9 | 41 |
| 13.8 | 30 |
| 17.3 | 29 |
| 19.4 | 25 |
| 21.3 | 29 |
| 21.6 | 56 |
| 22.0 | 41 |

Example 5: Pharmacokinetic Analyses

Methods:

A single oral, powder-in-capsule dose of each form was administered to three (n=3) female Sprague-Dawley rats and three male beagle dogs (n=3) at 5 mg active pharmaceutical ingredient per kg body weight. The plasma was then analyzed for compound plasma levels by LC/MS.

Preparation of Test Article for Capsule Dosing in Rats and Dogs:

Compound was milled using a mortar and pestle and was carefully dispensed into a gelatin capsule, tared on an analytical balance. Loading continued until the desired compound mass was achieved. Size 9 capsules were used for rat dosing and size 3 capsules were used for dogs. Note: compound load was corrected for the bioequivalence ratio of each form.

Following oral dosing, blood was drawn from the lateral saphenous vein into lithium heparin coated tubes (rats) or K$_2$EDTA coated tubes (dogs), at designated time points. Plasma was collected and stored frozen at −80° C. until analysis.

Rat Plasma Analysis:

Plasma samples (20 μL) and spiked plasma standard samples were diluted five-fold with ice cold acetonitrile containing 100 ng/mL verapamil as internal standard. Samples and standards were filtered through 0.22 m membranes in a 96-well format. Filtrates were then diluted with water to 30% acetonitrile.

10 μL of each sample and standard was injected onto a Waters Acquity CSH 1.7 m 2.1×100 mm column at 0.6 mL/min by an Acquity UPLC. The C18 column was equilibrated at 5% acetonitrile in water. Compounds were eluted with a gradient to 99% acetonitrile. All mobile phases contained 0.1% (v/v) formic acid.

HPLC Elution Gradient:

| Time (min) | % (v/v) Mobile Phase B |
|---|---|
| 0 | 5 |
| 0.75 | 5 |
| 1 | 20 |
| 4.5 | 99.9 |
| 5 | 99.9 |
| 5.4 | 5 |
| 6 | 5 |

Column eluent was analyzed by an electrospray ionization tandem quadrupole mass spectrometry system (ESI-MS/MS, a Waters Xevo TQ). Eluent composition was analyzed for three ion-pairs specific for the internal standard and three ion-pairs specific for the analyte. Experimental samples were compared with standard curve samples to determine compound concentrations. Pharmacokinetic parameters were determined using the Excel plug-in "PKfit".

Dog Plasma Analysis:

Plasma samples (20 μL) and spiked plasma standard samples were diluted eleven fold with ice cold acetonitrile containing 40 ng/mL Diclofenac as internal standard. The mixture was vortexed for 2 min and centrifuged. The 0.5 μL supernatant was injected into a Waters Acquity BEH 1.7 m 2.1×50 mm column at 0.6 mL/min by an Acquity UPLC. The column was equilibrated with 10% methanol in water. Compounds were eluted with a gradient to 95% methanol. Mobile phases contained 0.025% (v/v) formic acid and 1 mM NH$_4$OAc.

HPLC Elution Gradient:

| Time (min) | % (v/v) Mobile Phase B |
|---|---|
| 0 | 10 |
| 0.4 | 10 |
| 0.5 | 75 |
| 0.8 | 90 |
| 1.3 | 95 |
| 1.31 | 10 |
| 1.8 | 10 |

Column eluent was analyzed by an electrospray ionization tandem quadrupole mass spectrometry system (ESI-MS/MS, an API-6500). Eluent composition was analyzed for one ion-pairs specific for the internal standard and one ion-pairs specific for the analyte. Experimental samples were compared with standard curve samples to determine compound concentrations. Pharmacokinetic parameters were determined using WinNonlin Professional 6.2.

The co-crystal bisphosphate hemihydrate and hydrobromide salt of compound (I) display superior pharmacokinetics relative to the free base. The compounds were dosed orally as powder in capsule to Sprague Dawley rats and beagle dogs. As shown in Table 6, the bisphosphate hemihydrate co-crystal and crystalline hydrobromide salt of Compound (I) exhibit increased plasma concentrations relative to free base compound (I).

Table 6. Pharmacokinetic Parameters of Bisphosphate Demihydrate Co-crystal, Hydrobromide Salt and Free Base Compound (I) After PO Administration, Powder in Capsule, to Sprague-Dawley Rats and Beagle Dogs

| | $C_{max}$ (ng/mL) | | $AUC_{0-last}$ (ng·h/mL) | |
|---|---|---|---|---|
| | Rat | Dog | Rat | Dog |
| Compound (I) (5 mg/kg) | 11 | 8 | 140 | 40 |
| Compound (I) bisphosphate hemihydrate (5 mg/kg) | 1120 | 830 | 2100 | 4000 |
| Compound (I) hydrobromide (5 mg/kg) | 260 | 570 | 1640 | 2760 |

What is claimed is:

1. A method of treating a subject with cancer, comprising administering to the subject an effective amount of a co-crystal of compound (I) and a co-former molecule,

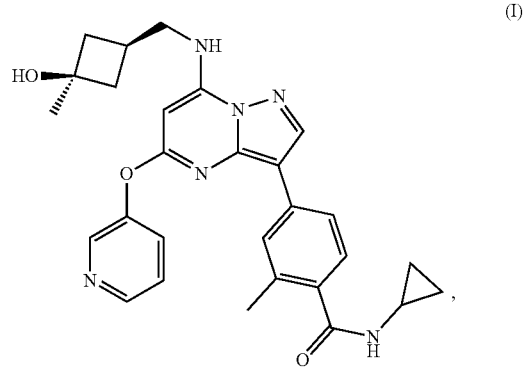 [SMILES: Cc1cc(-c2cnn3c(NC[C@H]4C[C@@](C)(O)C4)cc(Oc4cccnc4)nc23)ccc1C(=O)NC1CC1]

(I)

or a solvate of the co-crystal, wherein the co-former molecule is phosphoric acid, wherein the cancer is pancreatic cancer, prostate cancer, lung cancer, melanoma, breast cancer, colon cancer, ovarian cancer, hepatocellular carcinoma, mesothelioma, leukemia, lymphoma, or glioblastoma multiforme.

2. The method of claim 1, wherein the molar ratio of compound (I): phosphoric acid in the co-crystal is 1:2.

3. The method of claim 1, wherein the co-crystal is a hydrate, and the molar ratio of compound (I): phosphoric acid:H$_2$O in the co-crystal is 1:2:1/2.

4. The method of claim 1, wherein the co-crystal is characterized by any three, four or five of X-ray powder diffraction pattern peaks at 7.6°, 12.0°, 20.3°, 23.5°, and 24.5°±0.2 in 2θ.

5. The method of claim 1, wherein the co-crystal is characterized by X-ray powder diffraction pattern peaks at 7.6°, 12.0°, 20.3°, 23.5°, and 24.5°±0.2 in 2θ.

6. The method of claim 1, wherein the co-crystal is characterized by any three, four, five, six, seven, eight, nine, ten, or eleven of X-ray powder diffraction pattern peaks at 7.6°, 11.1°, 12.0°, 15.4°, 17.5°, 19.8°, 20.0°, 20.3°, 21.2°, 23.5°, 23.6°, and 24.5°±0.2 in 2θ.

7. The method of claim 1, wherein the co-crystal is characterized by X-ray powder diffraction pattern peaks at 7.6°, 11.1°, 12.0°, 15.4°, 17.5°, 19.8°, 20.0°, 20.3°, 21.2°, 23.5°, 23.6°, and 24.5°±0.2 in 2θ.

8. The method of claim 1, wherein the co-crystal is characterized by differential scanning calorimeter (DSC) peak phase transition temperatures of 160±4° C.

9. The method of claim 1, wherein a hydrogen bonding is formed between the hydrogen of the phosphoric acid and the nitrogen atom of the pyridine ring of compound (I) and the hydrogen bonding has a distance between 2.5-2.9 Å.

10. The method of claim 1, wherein the co-crystal is characterized by an $^{15}$N-Solid State Nuclear Magnetic Resonance Spectroscopy ($^{15}$N-ssNMR) peak at −122.5±2 ppm, and the intensity of the peak at −122.5 ppm is at least 40-70% less than the peak at −302 ppm.

11. The method of claim 1, wherein the cancer is lung cancer, breast cancer or colon cancer.

12. The method of claim 1, wherein the cancer is breast cancer.

13. A method of treating a subject with cancer, comprising administering to the subject an effective amount of a hydrobromide salt of compound (I) represented by the following structure formula:

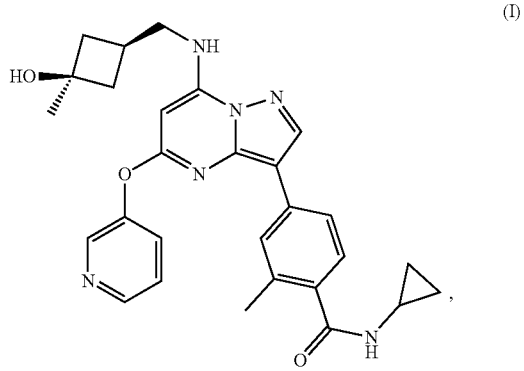 [SMILES: Cc1cc(-c2cnn3c(NC[C@H]4C[C@@](C)(O)C4)cc(Oc4cccnc4)nc23)ccc1C(=O)NC1CC1]

(I)

or a solvate thereof, wherein the molar ratio between compound (I) and hydrobromic acid is 1:1, wherein the hydrobromide salt is crystalline, and the crystalline hydrobromide salt is characterized by any three, four, five, six, seven, or eight of X-ray powder diffraction pattern peaks at 5.9°, 10.0°, 11.9°, 13.8°, 17.3°, 19.4°, 21.3°, 21.6°, and 22.0°±0.2 in 2θ, wherein the cancer is pancreatic cancer, prostate cancer, lung cancer, melanoma, breast cancer, colon cancer, ovarian cancer, hepatocellular carcinoma, mesothelioma, leukemia, lymphoma, or glioblastoma multiforme.

14. The method of claim 13, wherein the salt is in unsolvated form.

15. The method of claim 13, wherein the crystalline hydrobromide salt is characterized by three or four of X-ray powder diffraction pattern peaks at 5.9°, 11.9°, 21.6°, and 22.0°±0.2 in 2θ.

16. The method of claim 13, wherein the crystalline hydrobromide salt is characterized by X-ray powder diffraction pattern peaks at 5.9°, 10.0°, 11.9°, 13.8°, 17.3°, 19.4°, 21.3°, 21.6°, and 22.0°±0.2 in 2θ.

17. The method of claim 13, wherein the hydrobromide salt is characterized by differential scanning calorimeter (DSC) peak phase transition temperatures of 221±2° C.

18. The method of claim 13, wherein the cancer is lung cancer, breast cancer or colon cancer.

19. The method of claim 13, wherein the cancer is breast cancer.

* * * * *